United States Patent [19]

Adamich-Saltman

[11] Patent Number: 4,996,043

[45] Date of Patent: Feb. 26, 1991

[54] ADVANCED EQUINE HOOF PREPARATION

[75] Inventor: Marina Adamich-Saltman, Townsend, Del.

[73] Assignee: Equus Scientific Labs, Inc., West Coast Office, Woodside, Calif.

[21] Appl. No.: 889,409

[22] Filed: Jul. 21, 1986

[51] Int. Cl.$^5$ .................... A61K 7/04; A61K 31/715
[52] U.S. Cl. ........................................ 424/61; 514/54; 514/777; 514/782
[58] Field of Search .................. 424/61; 514/54, 777, 514/782

[56] References Cited

U.S. PATENT DOCUMENTS

| | | | |
|---|---|---|---|
| 2,887,116 | 5/1959 | Wooding | 424/61 X |
| 4,070,451 | 1/1978 | Price | 424/61 |
| 4,158,053 | 6/1979 | Greene et al. | 424/61 |
| 4,423,041 | 12/1985 | Clum et al. | 514/844 X |
| 4,478,853 | 10/1984 | Chaussee | 514/777 X |
| 4,530,828 | 7/1985 | Smith et al. | 424/61 |
| 4,661,343 | 4/1987 | Zabotto et al. | 514/844 X |

FOREIGN PATENT DOCUMENTS

| | | | |
|---|---|---|---|
| 673730 | 5/1963 | Canada | 514/777 |
| 2569347 | 2/1986 | France | 424/61 |

OTHER PUBLICATIONS

Okuyama, et al., Chem. Abs. 81, 16664c (1974).
Motoi, Chem. Abs., 105, 11860t (1986).
Motoi, Chem. Abs., 105, 120506c (1986).
Motoi, Chem. Abs. 105, 196994f (1986).
Hawley, The Condensed Chemical Dictionary, tenth edition, p. 431 (1981).

*Primary Examiner*—John W. Rollins
*Attorney, Agent, or Firm*—The Dulin Law Firm

[57] ABSTRACT

A composition for correcting dry hoof in equines and thereafter maintaining the hooves in healthy condition which comprises an aqueous dispersion of triglyceride, polysaccharide, silicone oil and an antifreeze and the process for using the composition which comprises applying the composition at least once a day to correct the condition and daily application thereafter to maintain the hooves in healthy condition.

20 Claims, No Drawings

ADVANCED EQUINE HOOF PREPARATION

FIELD OF THE INVENTION

This invention relates to a composition of matter useful for the maintenance and treatment of keratinous tissues and to a method for its use. More specifically this invention relates to materials useful to treat and maintain equine hooves in good condition.

BACKGROUND OF THE INVENTION

The equine hoof is a complex composite structure composed of soft (low sulfur) keratins and hard (high sulfur), tubular keratins embedded in a protein-keratin matrix. These components are structurally aligned in the hoof to absorb and dissipate the shock associated with the impact of a hoof with a surface, especially during running.

Keratin is a key component and imparts strength and flexibility to the hoof. The keratin must be maintained in a flexible state and kept from drying out and becoming brittle as it does in a condition called "dry hoof". This condition increases the tendency of the hoof to crack or break. If the hoof cracks or breaks it can result in injury to the animal. The key to keeping the keratin flexible is to keep it water balanced.

In the case of the horse, blood circulating through the hoof supplies sufficient nourishment and moisture to the hoof to maintain the keratin water balanced. Blood circulation through the hoof is lowered when the horse is standing still compared to circulation when the horse is walking and running because there are physical structures in the hoof that flex in response to the application and release to the horse's weight and thereby assist in the pumping of blood through the veins and arteries of the horse's leg. These physical structures include: the wall keratin and matrix protein which absorb and dissipate the shock of impact during running, a frog and sole which are keratinous and are located in the undersole of the hoof and which flex in response to walking and running, heel bulbs (also keratinous) which are located in the heel at the back of the horse's hoof and which flex outwardly when the horse's hoof strikes the ground, and the digital cushion, a vascularized area between the heel bulbs and the frog which compresses during walking and running. These structures cooperate to assist in circulating blood in the equine hoof in the following manner: when the hoof strikes the ground the keratin tubules and matrix absorb and transmit shock to the heel which expands outwardly, the frog and the sole expand downward, and the digital cushion compresses. This expansion and compression pumps venous blood, in the hoof, up the leg. Release of hoof from the surface returns the structures of the hoof to their rest position and arterial blood flows into the hoof. This pumping action increases the flow of blood through the hoof and thereby assures that nutrients and moisture is provided to the hoof which is vital to maintaining keratin flexibility.

When the keratin and matrix of the hoof become brittle, the heel bulb, frog, and wall expansion is diminished because the keratin does not flex as it normally does and has a tendency to crack or split. Additionally, a dry hoof does not dissipate the impact of the hoof's striking the ground in running as effectively as a natural, water balanced, flexible hoof. This condition, if untreated, can lead to numerous problems.

The healthy equine hoof has a relatively non-sticky surface which retards the adherence of dirt. This condition is augmented by the periople, which is a region of the hoof beginning at the coronary band and extending some variable distance downward. The function of the periople is to secrete a complex lipid film that spreads over the surface of the hoof to act as a moisture barrier. This lipid coating is also slippery and aids in preventing the adherence of dirt and foreign matter that might absorb the moisture from the hoof.

In their natural environment the horse is not immobilized for any duration and the hoof is not deprived of nourishment and moisture for an extended time. The situation is different for domesticated, stabled horses. When a horse is confined for an extended period of time the amount of blood circulating through its hoof is less than when the horse is moving. This results in less moisture passing to the keratin of the hoof. Additionally, a stall containing sawdust or other absorbant materials sets up a drying environment that dries the hoof's moisture and oil.

Other conditions contributing to the dry hoof problem include the rasping of the periople by the farrier, painting the hoof with drying chemicals such as organic solvents, lacquers, polishes and other agents, any abrasive substance contacting the hoof, and shoe nail holes, Repeatedly moving a horse having dry hooves to wet grounds or on to wet grass sets up a cycle which causes alternate swelling and contraction of the hoof wall leading to stress cracks.

Measures which might be regarded as remedial often exacerbate the problem. Application of lacquers and polishes in organic solvents to the hoof wall removes the lipid film and its beneficial effect. So rather than helping to prevent dry hoof they actually promote that condition.

Dry hoof causes a number of series problems for a horse: a brittle hoof may be difficult to shoe and does not hold a shoe well; the impact to the hoof when the hoof strikes the ground while running is not as efficiently dissipated by a brittle hoof which can lead to cracking of the hoof and lamness of the horse. These problems, if unattended, will eventually cause a great deal of pain and suffering to the horse as well as leaving it lame and potentially useless.

Prevention and correction of the "dry hoof" condition requires a composition and method which will:
1. Restore moisture lost by the hoof keratin,
2. Simulate the moisture barrier properties of the periople,
3. Maintain a non-sticky hoof surface
4. Avoid use of materials that build up on the hoof surface.

This invention meets these requirements and is effective in correcting a dry hoof condition and thereafter maintaining the hoof in a healthy water-balanced condition.

SCOPE AND CONTENT OF THE PRIOR ART

A large number of formulations are available which purport to remedy the dry hoof problem. Most of these formulations are based on the concept of sealing the surface of a hoof with the hope this will prevent water loss. The ingredients incorporated in these formulations include pine tars, pitch, waxes, creosol and various balsams. The solvents used to dissolve these ingredients include turpentine, organic solvents of all kinds and mineral oils. Additives include aloe, animal oils and fats, proteins, phospolipids and vitamins. These prior art formulations fail to remedy the dry hoof problem and in many cases make the situation worse. The organic solvents used to dissolve the tars and other substances applied remove the natural lipid film on the horse's hoof and any tar or pitch that remains on the hoof blocks the penetration of moisture from dew or other sources of moisture. All of these commercial formulations cause dirt and sawdust to adhere to the hoof. As this matter dries it absorbs water from the hoof and can lead to thrush, a decaying condition of the frog.

U.S. Pat. No. 2,887,116, issued to Wooding, describes a composition of nitrogenous resins that are applied to keratinous tissue as a dispersion. The invention is stated to be useful with hoofs and finger nails. The resins function to anchor other resins to the surface of the keratinous tissue. Thereafter lacquers are applied and improved bonding of the lacquer is observed. These compositions and the process described would actually be harmful to the hoof because they would prevent the natural lipids generated by the hoof from appearing on the hoof surface and would block the absorption of water from outside the hoof. This may not be a problem for the human subjects that are the obvious objects of the Wooding patent but would lead to dry hoof in the case of hooved animals.

A hoof care emulsion or cream is described in U.S. Pat. No. 4,070,451 issued to Price. This formulation contains a mixture of stearates and lanolin compounds which are applied as moisturizing oils. Price does not recognize the importance of polysaccharides, or triglycerides, nor especially triglycerides with a high degree of C18, monoenoic fatty acids, i.e., oleic acid component. The formulation is applied daily and must be massaged into the hoof wall, the hard sole, the frog and the coronet.

A number of patents describe formulations that are designed to be applied to finger nails. However, this art is not relevant to the subject matter of this invention because the environment of the hoof is considerably different than that of finger nails.

SUMMARY OF THE INVENTION

It has been found that most of the disadvantages of the prior art can be overcome using a formulation comprising an aqueous dispersion of oils high in monounsaturated fatty acid esters with an oleic:linoleic acid ester ratio of equal to or greater than one, and a water soluble or water swellable polysaccharide(s). Additional components include silicone oils, stabilizing agents, fragrances, glycols, buffers, sequesterants, antioxidants, antimicrobials, and fly repellents may also be incorporated into the formulation.

The formulation is applied to the horse's hoof and thereafter the hoof is wiped or buffed. This procedure insures that he water barrier coating is applied evenly to the surface and minimizes the ability of dirt and other moisture absorbing materials to cling to the hoof's surface.

DESCRIPTION OF THE PREFERRED EMBODIMENTS

The composition of this invention provides an aqueous dispersion useful for the treatment of keratinous tissues and which maintains keratinous tissue in a supple and water balanced state. The basic three components that comprise this invention, in percent by weight, encompasses the following ranges:

| Component | Percent by weight |
|---|---|
| Water | 20–90 |
| Polysaccharide | 0.1–3 |
| Triglyceride | 7–79.9 |

It is understood that the percentages of the three components above will total 100 percent by weight and if other materials are included in the formulation, the percentages of all ingredients will total 100 percent by weight.

The water component is preferably distilled or deionized but good quality tap water may also be utilized.

The polysaccharide component(s) singly or in combination is selected from the class of water soluble and water swellable polysaccharides which include xanthan gum, aliginates, arabinins, galactans, galactouranins, mannans, guar gums, carrageenan, alkyl and hydroxylalkylcellulose, carboxymethylcellulose, gum agar, gum arabic, gum Karaya, gum Traga canth, locust bean gum, pectins, starch and its derivatives and like compounds.

The triglyceride component(s) is selected from the class of oils derived from vegetable or animal origin and contain monounsaturated fatty acids with a content of at least 30 percent by weight of oleic acid. Linoleic acid ester is often found in triglycerides with oleic acid ester. In this invention the ratio of oleic:linoleic is maintained equal to or greater than one. This percentage and ratio apply regardless of whether the triglyceride is a single oil or a combination of oils. It will be understood that the term "oil" as used herein includes substances such as lard which are usually solid at room temperature. Representative examples of the vegetable and animal oils include, but is not limited to: cocoa butter, lard, neatsfoot oil, olive oil, palm oil, peanut oil, rice bran oil, sesame oil, tall oil and tallow. (Reference; Composition of Basic Oils, produced by Humko Chemical Division, Witco Chemical Corporation).

In addition to the basic three components, adjuvants may be added to further enhance to stabilize the basic three component formulation. Representative examples are listed below:

(a) Silicone fluids (polydimethylsiloxanes) from 10–2000 centistokes, and present from 0–10 percent by weight. Representative silicones are General Electric SF 96-50 which is a silicone fluid sold by General Electric Company and Dow 360 Medical Fluid which is sold by Dow Chemical Company.

(b) Lipids such as the amphiphilic phospholipids, sulpholipids and sterols such as cholesterol and related derivatives, such as cholesteryl sulphyate or cholesteryl esters, and the like and present at 0–5 percent by weight.

(c) Buffering agents that buffer in the range of pH 4 to 8 present from 0–2 percent by weight. Representative examples include; citric acid, sodium citrate, mixtures of mono and disodium phosphates, various acetate salts and HEPES buffer which is Sigma Chemical Company's tradename for its N-2-hydroxyethylpiperazine-N'-2-ethanesulfonic acid.

(d) Antioxidants present at concentrations of 0–2 percent by weight such as alpha-tocopherol, butylated hydroxytoluene, butylated hydroxyanisole and the like.

(e) Antimicrobial agents present at 0–2 percent by weight such as propyl and methylparabens, thimerisol, sodium nitrite, Dowicil 200, (Down Chemical Company's trademark for their antimicrobial agents) Germol 5, Germol 115 (Sutton Laboratories, Inc. trademark for their antimicrobial agents), chlorocetamide, and the like.

(f) sequestering agents present at 0–2 percent by weight such as ethylenediamine tetraacetic acid and its salts, and others.

(g) Fragrances and/or coloring agents, 0–0.5 percent by weight.

(h) Antifreeze to prevent freezing of the aqueous emulsion, 0–10 percent by weight. An example of said agent is propylene glycol.

(i) Fly repellant 0–0.5 percent by weight. Examples include citral, citronella, chrysanthemum oil and the like.

A more preferred embodiment of the invention comprises:

| Component | Percent by weight |
|---|---|
| Water | 30–80 |
| Polysaccharide | 0.2–2.0 |
| Triglyceride | 18–69.8 |

Where the water is preferably deionized or distilled water; the polysaccharide component singly, or in combination, is selected from the class of water soluble and water swellable polysaccharides which include xanthan gum, alginates, carrageenan, locust bean gum, and guar gum; and the triglyceride component(s) is selected from the class of oils derived from vegetable or animal origin, containing a high degree of monounsaturated fatty acids with a content of at least 30 percent by weight oleic acid, wherein the ratio oleic:linoleic is equal to or greater than one as the single oil component, or in combination with other oils selected from the group consisting of lard, neatsfoot oil, olive oil, palm oil, and peanut oil.

The adjuvants previously mentioned above may also be added to further enhance and or stabilize this embodiment and it is again understood that the components and the adjuvants are combined to give a total of 100 percent by weight.

A more highly preferred embodiment of the invention comprises:

| Component | Percent by weight |
|---|---|
| Water | 40–70 |
| Polysaccaharide | 0.3–1.0 |
| Triglyceride | 29.0–59.7 |

Where the water is preferably distilled or deionized water; the polysaccharide component singly, or in combination, is selected from the class of water soluble and water swellable polysaccharides which include xanthan gum, alginates, guar gum, and locust bean gum; and the triglyceride component(s) is selected from the class of oils derived from vegetable or animal origin, containing a high degree of monounsaturated fatty acids with a content of at least 40 percent by weight oleic acid and wherein the ratio oleic:linoleic is equal to or greater than 1.5:1, in the single component or in combination with other oils which includes lard, neatsfoot oil, olive oil, and peanut oil (Southwest).

The following adjuvants may optionally be added to enhance and further stabilize the basic three component formulation where the total percent by weight of the components and adjuvants combines to a total of 100 percent by weight:

(a) 0 to 5 percent by weight of silicon fluids (polydimethylsiloxanes) from 30–500 centistokes;

(b) 0 to 1 percent by weight of buffering agents including citric acid, sodium citrate, phosphates, acetates, HEPES buffer, and the like;

(c) 0 to 0.05 percent by weight of antioxidants including alpha-tocopherol, butylated hydroxytoluene, butylated hydroxyanisole and the like;

(d) 0 to 0.05 percent by weight of antimicrobial agents including propyl and methyl parabens, thimerisol, sodium nitrite Dowicil 200, Germol 5, Germol 115, chloroacetamide and the like;

(e) 0 to 0.05 percent by weight of sequestering agents including ethylenediamine tetraacetic acid and its salts; and (f) 0 to 10 percent by weight of antifreeze such as propylene glycol.

The most preferred embodiment of the invention comprises:

| Component | Percent by weight |
|---|---|
| Water | 45–55 |
| Polysaccharide | 0.4–0.8 |
| Triglyceride | 44.2–54.6 |

Where the water is preferably deionized or distilled water; the polysaccharide is xanthan gum; and the triglyceride components(s) is selected from the class of oils derived from vegetable or animal origin, containing a high degree of monounsaturated fatty acids with a content of at lest 40 percent by weight of oleic acid, wherein the ratio oleic:linoleic is equal to or greater than 1.5:1 in the single oil component, or in combination with the other oils selected from the group consisting of neatsfoot oil, olive oil, or peanut oil (Southwest). This most preferred embodiment may optionally contain adjuvants to further enhance or stabilize the invention and includes the following material where it is understood that the total percentage of the formulation is 100 percent by weight:

(a) 0 to 2 percent by weight of silicone fluids (polydimethylsiloxanes) whose viscosity ranges from 30–350 centistokes;

(b) 0 to 1 percent by weight of buffering agents including citric acid, sodium citrate, phosphates, acetates and HEPES buffer;

(c) 0 to 0.5 percent by weight of antioxidants including alpha-tocopherol, butylated hydroxytoluene, butylated hydroxyanisole and the like;

(d) 0 to 0.5 percent by weight of antimicrobial agents including propyl and methyl parabens, thimerisol , sodium nitrite, Dowicil 200, Germol 5, Germol 115, chloroacetamide and the like;

(e) 0 to 0.5 percent by weight of sequestering agent including ethylenediamine tetraacetic acid and it salts and the like; and (f) 0 to 7.5 percent by weight of propylene glycol.

The method of using the invention involves applying the embodiments for application to keratinous tissue, e.g. horse's hooves, in which the hoof is treated with the formulation and then wiped or buffed. This procedure ensures a uniform coating with water-barrier properties, and which diminishes surface-cling of material to the hoof.

EXAMPLE 1

To a Waring blender was added deionized water (1 cup, 225g, 5.16 percent by weight), HEPES buffer (2 spoonfuls, 1.9g, 0.4 percent by weight) and they were mixed for 3 minutes at the blend setting. Next, ethylenediamine tetraacetic acid (½ spoonful, 0.4g, 0.1 percent by weight) and butylated hydroxytoluene (½ spoonful, 0.6g, 0.2 percent by weight) were tapped in during blending, followed by a gentle sifting of Xanthan gum (3 spoonfuls, 3.3g, 0.8 percent by weight). Then, peanut oil (1 cup, 204g, 46.8 percent by weight) was slowly poured into the vortex during high shear mixing on the blend setting followed by pulses on the beat setting.

This composition was tested in Field Trials on horse's hooves from different equine breeds, environmental conditions, e.g., stabling and seasons. The results showed significant benefits compared to non-treated controls. This formulation resulted in a cleaner hoof surface, enhanced natural hoof color and sheen, and increased suppleness of the frog, heel bulbs, coronary band, while maintaining a resilient horn (hoof wall). It was noticed that packed dirt in the sole crumbled out easily on picking the hoof, and also, the hoof surfaces remained free of clinging dirt just as the surface of healthy natural hoof.

EXAMPLE 2a.

The procedure of example 1 was repeated except that silicon oil (General Electric SF 96–50; 50 centistokes) (2 ml, 1.97g, 0.45 percent by weight) was added by mixing with the peanut oil by swirling the oils together before they were added to the vortex as described in Example 1. This formulation was tested on different horses, representing distinct breeds, and stabling conditions. IT was observed that this formulation enhanced the cleanliness (decreased surface-cling of dirt and other materials, and hoof coloration while horses were stabled. The silicon oil aids in the retention of the applied formulation during stabling, but is removed by natural abrasion on turn-out or exercise.

EXAMPLE 2b.

Silicone oil (General Electric SF 96–50: 50 centistokes) was increased threefold and added to the formulation in the manner described in Example 2a, namely 5.9g, representing 1.33 total percent by weight silicone oil. When this formulation was tested on equines, the results indicated a further enhancement in natural hoof coloration and diminished surface-cling of dirt during stabling.

COMPARATIVE EXAMPLE 2

The following formulation was prepared according to Example 2a, except that corn oil was exchanged for peanut oil (Example 2a), 46.6 percent by weight triglyceride content. This formulation was tested and found to be ineffective in moisturizing and improving the quality of the hoof, compared to the composition of Example 2a. The importance of the oleic acid ester content and linoleic acid ester contents are noted: corn oil contains approximately 30% oleic and 56% linoleic acid ester while peanut oil used in the formulations described in this invention, contains some 50% oleic and only 30.5% linoleic. Furthermore, the ratio oleic:linoleic acid ester in corn oil is less than 1 while for peanut oil, it is greater than 1.

EXAMPLE 3

This formulation was prepared according to procedures described in Example 2b with the following modifications: The triglyceride component included peanut oil and olive oil. The olive oil was present at 16.25 percent by weight of the entire formulation and the peanut oil present at 28.37 percent by weight. The total triglyceride content 44.62 percent by weight. Additionally, fragrance 2,3, butanendione (0.1 percent by weight) and fly repellant, citral (0.05 percent by weight) were added. Testing of this formulation on horse's hooves indicated that not only was the hoof color enhanced, and heel and frog suppleness improved, but shoes did not loosen from hooves, and a significant decrease in thrown shoes was noted.

EXAMPLE 4

Horses stabled on straw or large wood shavings and treated with Example 1 through 3 formulations were observed to have relatively dirt-free hooves, with a response time of about 2–2 weeks for enhanced coloration of the natural hoof, smooth texture, and suppleness of frog, heel and coronary band. On extra fine wood shavings, i.e. sawdust, equine hooves took significantly longer to respond to the above formulations. Fine shavings appeared to adhere to the hoof and would tend to increase moisture loss due to its high absorptive properties. It was found that the "sawdust surface" effect could be overcome by the following procedure which significantly reduces the surface-cling of foreign matter of the hoof.

Step 1. Hooves are picked clean and washed with water to remove excess debris from hooves.

Step 2. The formulation is applied to the hooves with a paint brush, hand, or cloth.

Step 3. The formulation is allowed to remain on the hoof for at least 5 minutes and then wiped or buffed off the entire hoof surface.

A comparative study was made by painting half of one hoof with formulation described in Example 3, and the other hand is painted with a commercially available preparation. The procedures described for each commercial preparation is followed. Next, a handful of sawdust is thrown against the hoof and a photograph is taken. The control hoof which remained untreated was given a surface-cling value of zero, with maximum surface cling having a value of 10. As can be seen from the following table, the Example 3 formulation was found for surface cling value of zero and is comparable to the control equine hoof.

| Hoof Conditioner | Rating |
| --- | --- |
| Control hoof | 0 |
| Bickmore | 10 |
| Hooflex | 9 |
| Super Hoof | 6 |
| Aloe Hoof | 3 |
| Example 3 formulation | 0 |

EXAMPLE 5 to a 1,000 gallon tank is added 1282 liters of deionized water (47.48 percent by weight), 0.864 kg. of citric acid (.032 percent by weight), 2.51 kg of sodium citrate (0.093 percent by weight) and ethylenediamine tetraacetic acid disodium salt (2.51 kg, 0.093 percent by weight). After mixing the pH was determined to be 5.7. Propylene glycol (146.15 kg, 5.41 percent by weight) containing a slurry of Keltrol Xanthan Gum (2.997 kg, 0.111 percent by weight), methyl paraben (2,997 kg, 0.111 percent by weight) and propyl paraben (1.593 kg, 0.059 percent by weight) is added with mixing. After homogeneity is reached, peanut oil (716.5 kg, 26.54 percent by weight), olive oil (487.43 kg, 18.05 percent by weight) and silicon oil (Dow 360 Medical Fluid: 100 centistokes)(38.99 kg, 1.444 percent by weight) are added and thoroughly mixed.

The formulation of this invention was applied to a horse having a dry hoof condition and a tendency to loose shoes. Daily application, as described above, of the composition mode of the invention was done for three weeks. At the end of this period there was a noticeable improvement of the dry hoof condition ed suppleness of the frog and heel bulbs. Thereafter application of this composition was continued several times a week and after two months horse's tendency to lose shoes was eliminated and the hooves were a darker natural color, smoother textured and with no noticeable surface-cling of sawdust or other moisture absorbing materials. The greatest improvement was in the absence of splitting or cracking of the hoof and on reshoeing the horse it was possible to use the same nail holes that were made previously. This latter observation is especially noteworthy because ususally the farrier must make new holes on reshoeing. In this case it was observed that the old holes were able to accept the nails with sufficient friction to hold the shoe on. There was no difficulty with the horse losing shoes afterward. Frequent application, i.e., three to five times a week during the following years resulted in the healthy condition of the hooves being maintained with out loss of shoes.

Other variations within the scope of this invention will be apparent to those skilled in the art.

I claim:

1. A composition for the veterinary prophylaxis and treatment of ungular keratinous tissue to ameliorate dry hoof condition, said composition being an aqueous dispersion consisting essentially of:
   (a) 20 to 90 percent by weight of water;
   (b) 0.1 to 3 percent by weight of polysaccharide;
   (c) 7 to 79.1 percent by weight of triglyceride;
   (d) at least 30 percent by weight of the fatty acid of said triglyceride is oleic acid, and the ratio oleic acid:linoleic acid is equal to or greater than 1;
   (e) said composition exhibiting properties when applied to keratin-containing non-skin, non-hair ungular tissue of:
      (i) a non-sticky surface to reduce adhesion of moisture-absorbing substances such as dirt and sawdust;
      (ii) restoring moisture;
      (iii) simulating periople moisture barrier;
      (iv) aiding in prevention of stress cracks and brittleness
      (v) non-drying; and
      (vi) not permanently retarding lipid film development; and
   (f) whereby application to complex composite ungular keratin-containing tissue structures restores them to and maintains them in a healthy water-balanced condition.

2. A veterinary dry hoof prophylaxis and treatment composition according to claim 1 wherein:
   (a) said water is present in the range of from about 30 to 80 percent by weight;
   (b) said polysaccharide is present in the range of from about 0.2 to 2 percent by weight; and
   (c) said triglyceride is present in the range of from about 18 to 69.8 percent by weight.

3. The veterinary dry hoof prophylaxis and treatment composition of claim 2 in which:
   (a) the triglyceride is 16.25 percent by weight of olive oil and 28.37 percent by weight of peanut oil;
   (b) the total triglyceride content is 44.62 percent by weight; and
   (c) which contains 0.1 percent by weight of 2,3-butanedione, and 0.05 percent by weight of citral.

4. A veterinary dry hoof prophylaxis and treatment composition according to claim 1 wherein:
   (a) said water is present in the range of from about 40 to 70 percent by weight;
   (b) said polysaccharide is present in the range of from about 0.3 to 1 percent by weight;
   (c) said triglyceride is present in the range of from about 29.0 to 59.7 percent by weight; and
   (d) at least 40 percent by weight of the fatty acid of said triglyceride is oleic acid, and the ratio oleic acid:linoleic acid is equal to or greater than 1.5 :1.

5. A veterinary dry hoof prophylaxis and treatment composition according to claim 1 wherein:
   (a) said water is present in the range of from about 45 to 55 percent by weight;
   (b) said polysaccharide is present in the range of from about 0.4 to 0.8 percent by weight;
   (c) said triglyceride is present in the range of from about 44.2 to 54.6 percent by weight; and
   (d) at least 40 percent by weight of the fatty acid of the triglyceride is oleic acid, and the ratio oleic acid;linoleic acid is equal to or greater than 1.5 to 1.

6. A composition according to claim 1, 2, 4 or 5 which contains less than about 10 percent by weight of a silicone fluid.

7. A composition according to claim 1, 2, 4 or 5 which contains less than about 10 percent by weight of antifreeze.

8. A composition according to claim 1, 2, 4 or 5 which contains less than about 5 percent by weight of a lipid.

9. A composition according to claim 1, 2, 4 or 5 which contains less than about 0.5 percent of fly repellant.

10. A composition according to claim 5 which contains less than about 1 percent by weight of a buffering agent.

11. A composition according to claim 5 which contains less than about 2 percent by weight of an antioxidant.

12. A composition according to claim 5 which contains less than about 2 percent by weight of an antimicrobial agent.

13. A composition according to claim 5 which contains less than about 2 percent by weight of a sequestering agent.

14. A veterinary dry hoof prophylaxis and treatment composition according to claim 4 which consists essentially of:
   (a) 51.6 percent by weight of water;
   (b) 0.8 percent by weight of xanthan gum;
   (c) 46.8 percent by weight peanut oil;
   (d) 0.1 percent by weight of N-2-hydroxyethylpiper azine-N'2-ethanesulfonic acid;

(e) 0.2 percent by weight of butylated hydroxytoluene; and (f) 0.1 percent by weight of ethylenediamine tetraacetic acid.

15. The veterinary dry hoof prophylaxis and treatment composition of claim 14 which includes 0.4 percent by weight of silicone oil.

16. The veterinary dry hoof prophylaxis and treatment composition of claim 14 which includes 1.33 percent by weight of silicone oil.

17. A method for maintaining ungular, non-skin, non-hair keratinous tissue in healthy condition substantially free of dry hoof condition which comprises the steps of:
  (a) providing an aqueous dispersion composition consisting essentially of:
    (i) 20 to 90 percent by weight of water;
    (ii) 0.1 to 3 percent by weight of polysaccharide;
    (iii) 7 to 79.9 percent by weight of triglyceride; and wherein at least 30 percent by weight of the triglycerides is oleic acid; and
  (b) applying an effective amount of said dispersion composition on keratinous ungular tissue to maintain said structure in said healthy condition substantially free of said dry hoof condition.

18. A dry hoof prophylaxis method according to claim 17 wherein:
  (a) said dispersion composition includes:
    (i) less than about 10 percent by weight of silicone oil; and
    (ii) less than about 10 percent by weight of antifreeze; and
  (b) said composition is applied in an amount to render said keratinous ungular tissue resistant to the adherence of moisture absorbing foreign matter.

19. A method for correcting a dry hoof condition in a horse which comprises applying to the hoof of a horse with a dry hoof condition an effect amount of an aqueous dispersion containing:
  (a) 20 to 90 percent by weight of water;
  (b) 0.1 to 3 percent by weight of polysaccharide;
  (c) 7 to 79.9 percent by weight of triglyceride;
  (d) 0 to 10 percent by weight of silicone oil; and
  (e) 0 to 10 percent by weight of antifreeze: then buffing or wiping the hoof to remove excess dispersion said procedure to be done at least once a day and continued until the condition is corrected.

20. A method for treating dry hoof condition which comprises the steps of:
  (a) providing an aqueous dispersion containing:
    (i) 20 to 90 percent by weight of water;
    (ii) 0.21 to 3 percent by weight of polysaccharide;
    (iii) 7 to 79.9 percent by weight of triglyceride;
    (iv) less than about 10 percent by weight of silicone oil; and
    (v) less than 10 percent by weight of antifreeze; and
  (b) applying an effective amount of said aqueous dispersion composition to the affected surface exhibiting said dry hoof condition for a time sufficient to ameliorate said dry hoof condition.

* * * * *